US011925715B2

(12) United States Patent
McGill et al.

(10) Patent No.: US 11,925,715 B2
(45) Date of Patent: Mar. 12, 2024

(54) APPARATUS AND METHOD FOR PROVIDING STERILIZATION IN COMPACT FORM

(71) Applicants: Jean Seibold McGill, Easton, PA (US); James Noah McNeely, Grayson, GA (US)

(72) Inventors: Jean Seibold McGill, Easton, PA (US); James Noah McNeely, Grayson, GA (US)

(73) Assignee: Clean Case LLC, Easton, PA (US)

( * ) Notice: Subject to any disclaimer, the term of this patent is extended or adjusted under 35 U.S.C. 154(b) by 396 days.

(21) Appl. No.: 17/249,419

(22) Filed: Mar. 2, 2021

(65) Prior Publication Data
US 2022/0023462 A1 Jan. 27, 2022

Related U.S. Application Data

(60) Provisional application No. 62/705,990, filed on Jul. 24, 2020.

(51) Int. Cl.
*A61L 2/10* (2006.01)
*A61L 2/26* (2006.01)

(52) U.S. Cl.
CPC ............... *A61L 2/10* (2013.01); *A61L 2/26* (2013.01); *A61L 2202/11* (2013.01); *A61L 2202/122* (2013.01); *A61L 2202/14* (2013.01); *A61L 2202/16* (2013.01); *A61L 2202/21* (2013.01)

(58) Field of Classification Search
CPC .......... A61L 2/10; A61L 2/26; A61L 2202/11; A61L 2202/122; A61L 2202/14; A61L 2202/15; A61L 2202/21
See application file for complete search history.

(56) References Cited

U.S. PATENT DOCUMENTS

| 7,547,893 | B1 | 6/2009 | Tantillo |
| 7,646,000 | B2 | 1/2010 | Shih |
| 7,888,656 | B2 | 2/2011 | Freedgood |
| 8,399,853 | B2 | 3/2013 | Roiniotis |
| 8,685,318 | B2 | 4/2014 | Collard et al. |
| 8,841,632 | B1 | 9/2014 | Griffin et al. |
| 9,000,398 | B2 | 4/2015 | Nelson et al. |
| 10,603,394 | B2 | 3/2020 | Farren et al. |
| 2002/0146343 | A1 | 10/2002 | Jenkins et al. |
| 2004/0155201 | A1* | 8/2004 | Russell ............... A61L 2/10 250/455.11 |
| 2006/0242788 | A1 | 11/2006 | Day |

(Continued)

FOREIGN PATENT DOCUMENTS

WO WO-2021071023 A1 * 4/2021 .......... A45C 11/005

*Primary Examiner* — Jennifer Wecker
*Assistant Examiner* — Brady C Pilsbury
(74) *Attorney, Agent, or Firm* — Dunlap Bennett & Ludwig, PLLC

(57) ABSTRACT

A sterilization system and method for sterilizing an oral appliance is disclosed. As part of the system, a sterilization case is provided, which includes a case body, a rechargeable battery, and at least one ultraviolet light. The case body includes a top portion and a bottom portion movably connected to one another, and the case body is sized and shaped to house the oral appliance. The at least one ultraviolet light is mounted in the case body, is powered by the rechargeable battery, and, in use, sterilizes the oral appliance.

1 Claim, 4 Drawing Sheets

(56) References Cited

U.S. PATENT DOCUMENTS

| | | |
|---|---|---|
| 2009/0226241 A1 | 9/2009 | McEwen et al. |
| 2010/0203464 A1 | 8/2010 | Nevin |
| 2010/0260648 A1 | 10/2010 | Lin |
| 2016/0317268 A1 | 11/2016 | Dietzel et al. |
| 2018/0014380 A1* | 1/2018 | Kornicki .............. A61C 17/036 |
| 2018/0117191 A1 | 5/2018 | Shell |
| 2020/0022483 A1* | 1/2020 | Pierce .................... A61C 19/02 |

* cited by examiner

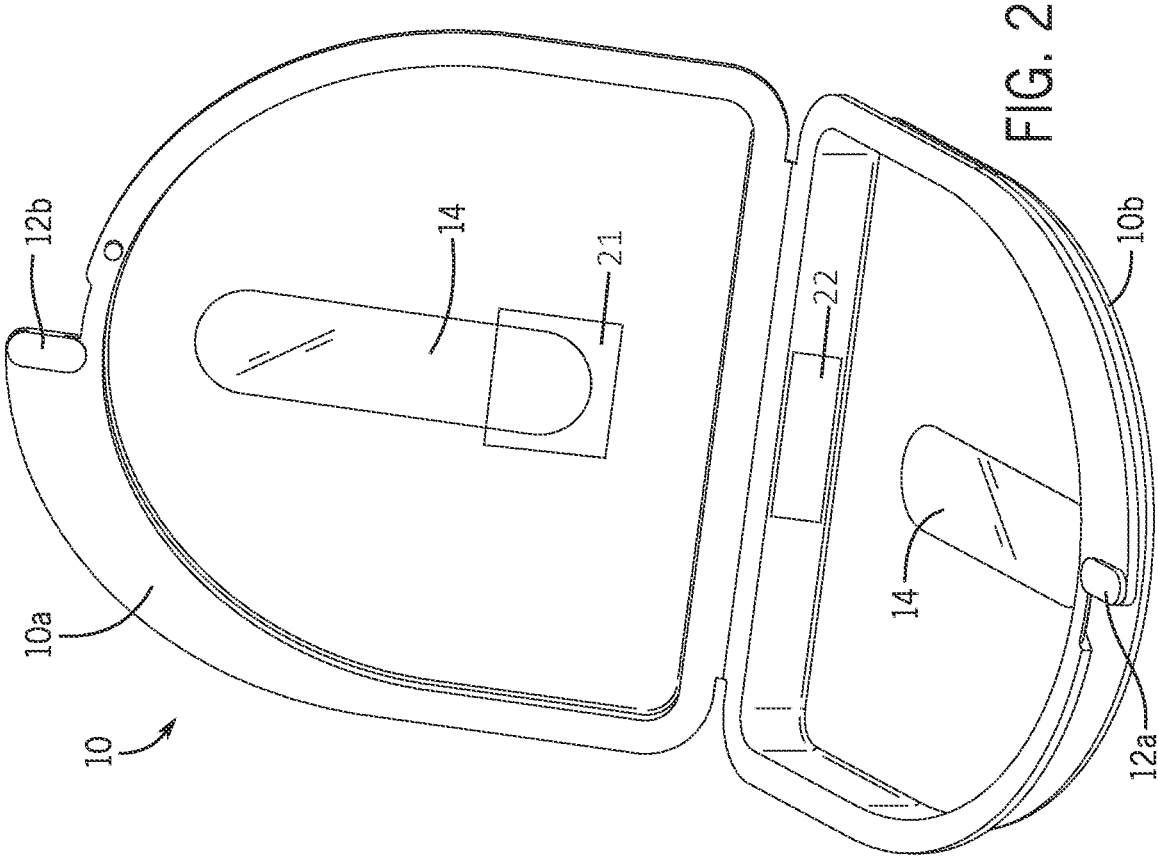
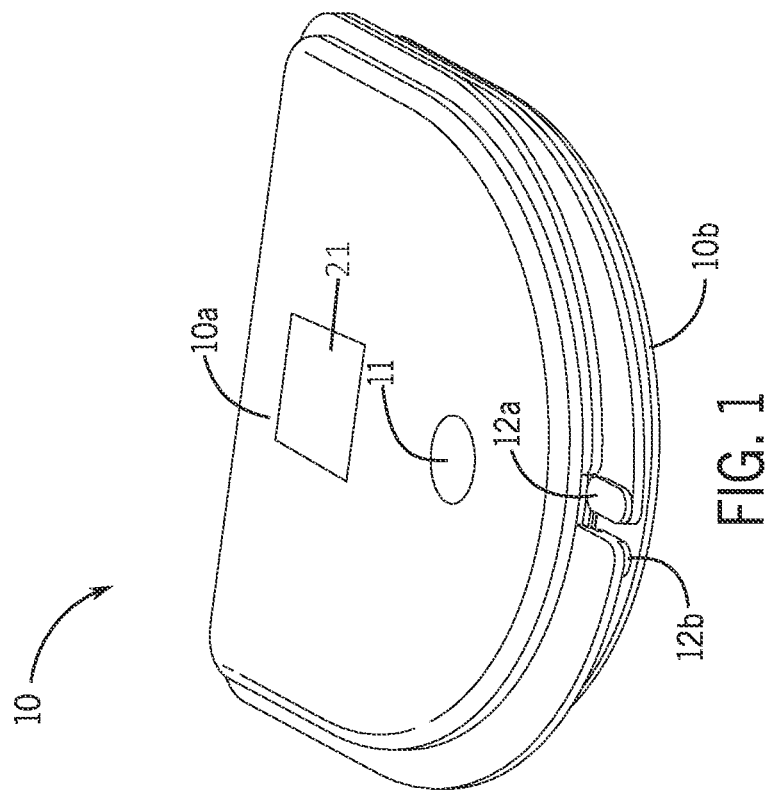

US 11,925,715 B2

APPARATUS AND METHOD FOR PROVIDING STERILIZATION IN COMPACT FORM

CROSS-REFERENCE TO RELATED APPLICATION

This application claims the benefit of priority of U.S. provisional application No. 62/705,990, filed Jul. 24, 2020, the contents of which are herein incorporated by reference.

BACKGROUND OF THE INVENTION

The present invention relates to sterilization cases and, more particularly, to a rechargeable, portable ultraviolet (UV) sterilization case for oral appliances, such as retainers or aligners, for example.

Coronavirus disease 2019 (COVID-19) has generally increased awareness for the need to sterilize items used personally. Patients using oral appliances (such as retainers, aligners, dentures, etc.) need easy sterilization of these appliances on the go. These oral appliances collect bacteria, plaque, and other pathogens while individuals wear them, and they don't go away unless cleaned/sanitized properly. Remembering or taking the time to clean the oral appliance can be a challenge for many wearers, which results in these pathogens/bacteria continuing their growth on the oral appliance, even while not in use.

Sterilization cases designed specifically for phones exist in some form, but these are not ideal because they are very bulky and not suitable for oral appliance sterilization when is someone is out and about (i.e., they are not readily portable). These and other cases are simply too large and not portable enough for oral appliances, which are often carried in a small space, like a pocket. Further, bathrooms are often limited in space, meaning an oral appliance case must also be sized to fit in a bathroom cabinet, which even further highlights the need for a sterilization case that is compact.

As can be seen, there is a need for a rechargeable, portable UV sterilization case for oral appliances.

SUMMARY OF THE INVENTION

In one aspect of the present invention, a sterilization case includes: a case body including a top portion and a bottom portion movably connected to one another, the case body being sized to house an oral appliance; a rechargeable battery; and at least one ultraviolet light mounted in the case body and being powered by the rechargeable battery, the at least one ultraviolet light being configured to sterilize the oral appliance.

In another aspect of the present invention, a sterilization system includes: an oral appliance; and a sterilization case including: a case body including a top portion and a bottom portion movably connected to one another, the case body being sized to house the oral appliance; a rechargeable battery; and at least one ultraviolet light mounted in the case body and being powered by the rechargeable battery, the at least one ultraviolet light being configured to sterilize the oral appliance.

In yet another aspect of the present invention, a method of sterilizing an oral appliance includes the steps of: (1) providing a sterilization case including: a case body including a top portion and a bottom portion movably connected to one another, the case body being sized to house an oral appliance; a rechargeable battery; and at least one ultraviolet light mounted in the case body and being powered by the rechargeable battery, the at least one ultraviolet light being configured to sterilize the oral appliance; (2) opening the sterilization case; (3) inserting the oral appliance; (4) closing the sterilization case; and (5) inserting the sterilization case into a pant pocket.

These and other features, aspects and advantages of the present invention will become better understood with reference to the following drawings, description and claims.

BRIEF DESCRIPTION OF THE DRAWINGS

FIG. 1 is a perspective view of an embodiment of the present invention, shown in a closed position;

FIG. 2 is another perspective view of the embodiment of the present invention, shown in an open position;

DETAILED DESCRIPTION OF THE INVENTION

Figure 3:
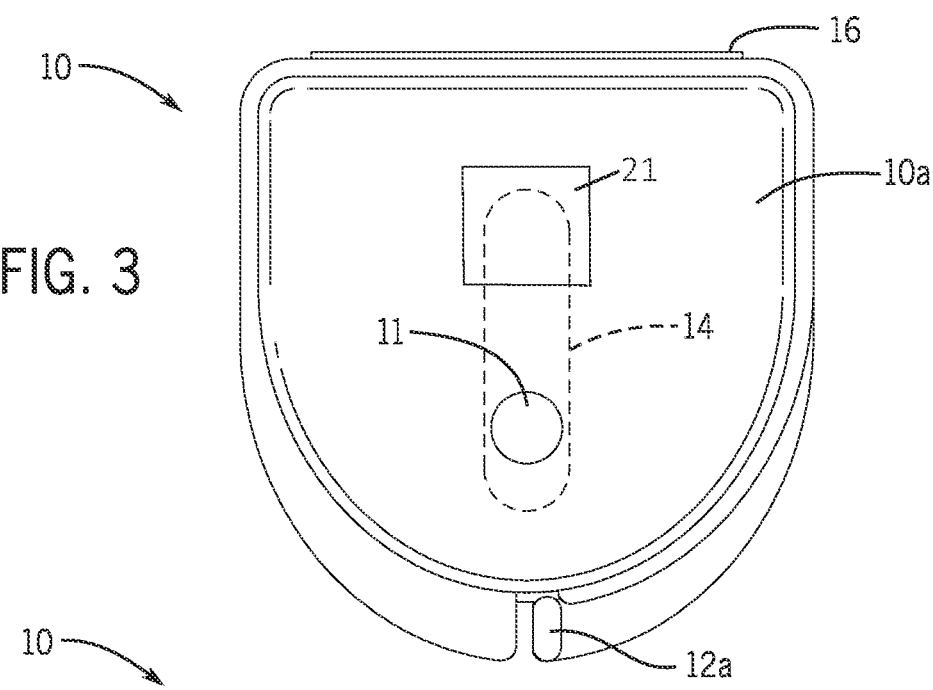
FIG. 3 is a top plan view of the embodiment of the present invention, showing a UV bulb in phantom lines.
Figure 4:
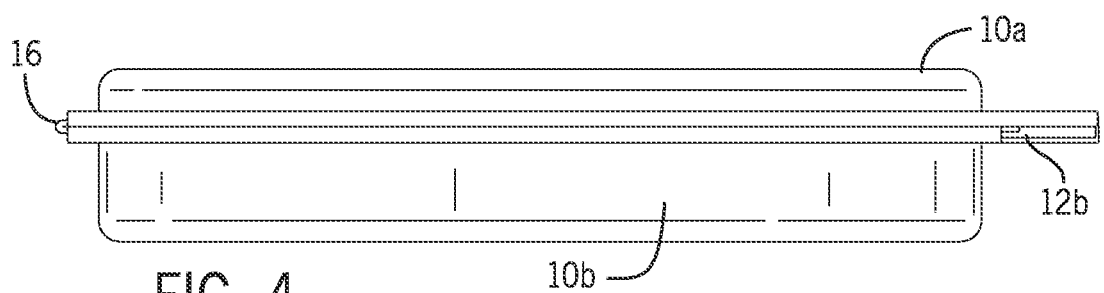
FIG. 4 is a left side elevation view of the embodiment of the present invention.

The following detailed description is of the best currently contemplated modes of carrying out exemplary embodiments of the present invention. The description is not to be taken in a limiting sense but is made merely for the purpose of illustrating the general principles of the present invention, since the scope of the present invention is best defined by the appended claims.

Broadly, an embodiment of the present invention provides a sterilization case configured for sterilizing oral appliances, the sterilization case comprising: a case body including a top and a bottom hingedly/movably connected to one another, the case body being sized to house at least one of a retainer, an aligner, or a denture (i.e., an oral appliance), or a pair of contacts; a rechargeable battery; and at least one ultraviolet light mounted in the case body and being powered by the rechargeable battery, the at least one ultraviolet light being configured to sterilize the at least one of the retainer, the aligner, the denture, or the pair of contacts.

One embodiment of the present invention is a small rechargeable portable travel case so that people can sterilize their appliances. In accordance with certain aspects of the present invention, the travel case is configured for oral appliances and is portable. The embodiment is small and may take a similar form/size as a retainer case and may fit in a user's pocket (such as a pocket in a pair of pants). This may, in particular, be suitable for a child patient, but may be used by anyone who needs to transport an oral appliance. Important aspects of the present invention include a case (formed from, for example, plastic), a rechargeable UVC bulb, and an external charging cord.

Referring now to FIGS. 1-7, certain embodiments of the present invention include a re-chargeable sterilization case 10 that has a body with a top portion 10a and a bottom portion 10b hingedly connected to one another via, for example, a living hinge 16. As seen, for example, in FIGS. 1-3, the top portion 10a and the bottom portion 10b each define a substantially linear peripheral edge proximal the living hinge 16 and a substantially arcuate peripheral edge distal the living hinge 16, thus closely resembling the appearance of an oral appliance case. The arcuate edge allows for a reduction in material because it follows the contour of the oral appliance it is housing. It will be appreciated by those with skill in the art that other appropriate designs for opening and closing the case 10 may be employed. The sterilization case, by its compact design, is highly portable and may be used for oral appliances and the like. As shown in FIGS. 1-2, it may even be designed to resemble a conventional retainer/denture case. The sterilization case 10 may be retained closed by a first closure tab 12a and a second closure tab 12b, as shown in FIG. 1.

UV bulbs 14 of the present invention may be selectively powered on and off by a power button 11. The power button 11 may include an internal timer for automatically controlling the amount of time the UV bulbs are on for. While the power button 11 has been shown on the top of the sterilization case 10 in the presently illustrated embodiment, its location may be moved in accordance with the present invention as appropriate or needed. The UV bulbs 14 may be disposed on the top portion 10a and bottom portion 10b to effectively sterilize both sides of the oral appliance, as shown in FIG. 2. In certain embodiments, the UV bulbs 14 may be embedded in the top portion 10a and bottom portion 10b. In use, the sterilization case 10 may run for approximately ten minutes and shut off when the sterilization cycle has been completed. The period that the sterilization case 10 runs for may be modified in accordance with the present invention such that sufficient sanitization of the oral appliance occurs. In certain embodiments, a failsafe shutoff may be provided such that power to the sterilization case 10 is shut off when a user opens the case mid-cycle.

As shown in FIGS. 1-3, a transparent or translucent piece of see-through material 21 (such as plastic) may be provided on the top portion 10a of the case 10. Advantageously, the see-through material 10 is located proximal to or at least partially overlaps one of the UV bulbs 14, which results in a "glow" effect when the UV bulbs 14 are powered on. Thus, this serves as a visual cue to the user the UV bulbs 14 are still active, and that the case 10 shouldn't be opened until the cycle has completed. In embodiments that incorporate the see-through material 10, it is embodied such that the material blocks and/or absorbs the frequencies of UV light that should not escape the case 10.

Figure 5:
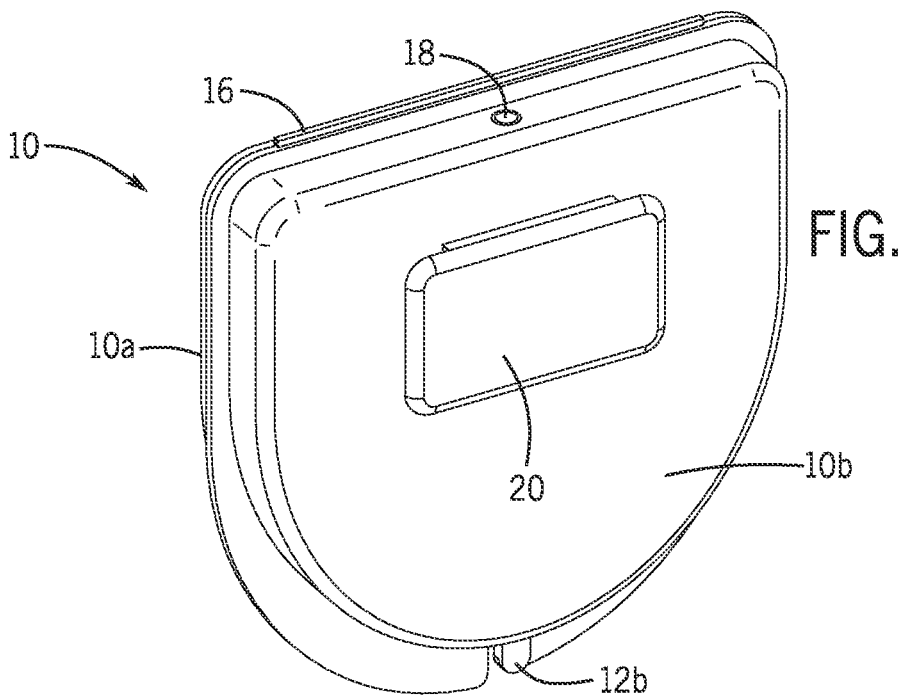
FIG. 5 is a bottom perspective view of the embodiment of the present invention.
Figure 6:
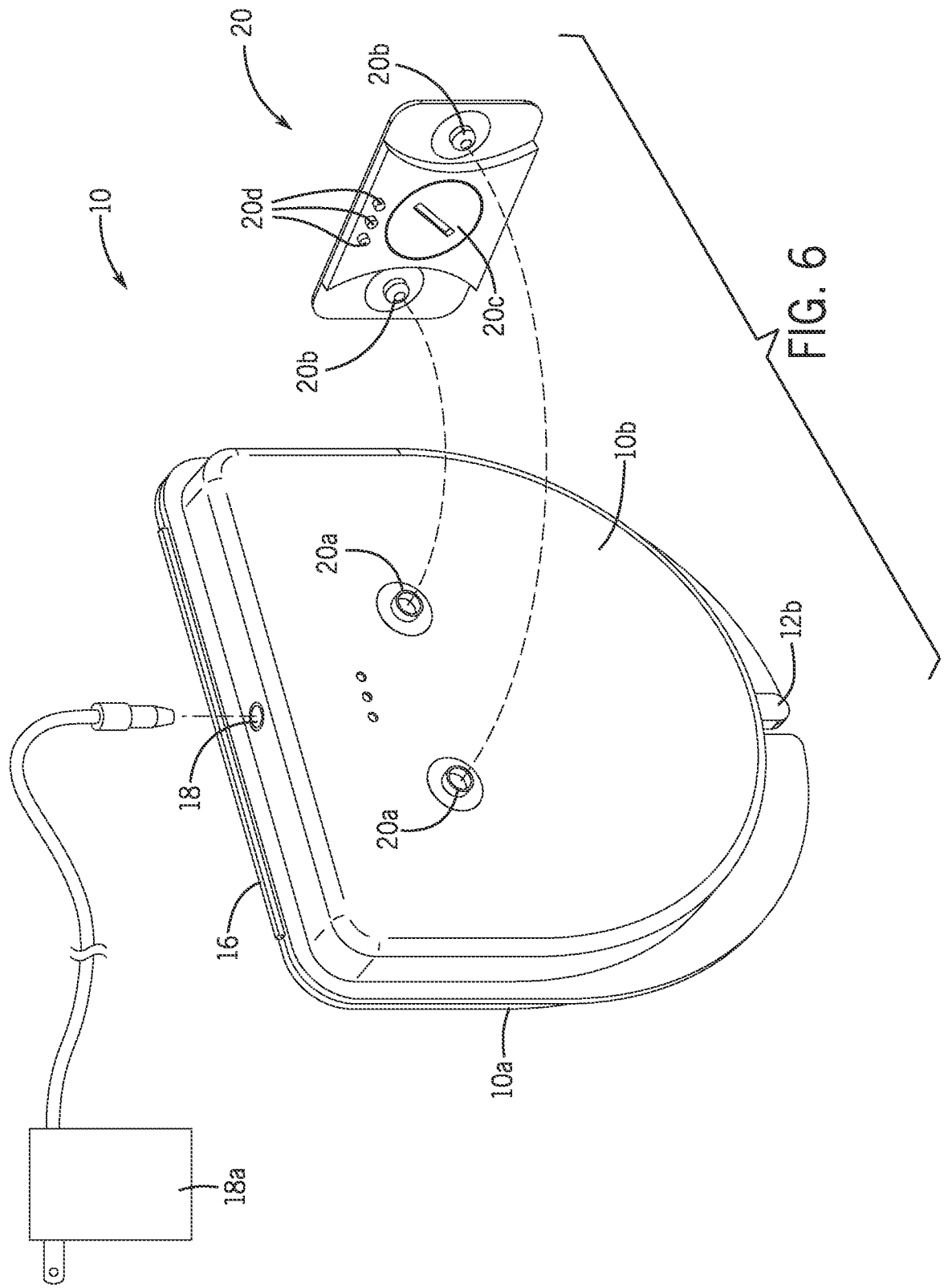
FIG. 6 is an exploded perspective view of the embodiment of the present invention.

As shown in FIG. 5, a power port 18 (such as, but not limited to, an AC power port) may be provided on the bottom 10b of the sterilization case 10, which couples with a power adapter 18a to charge a rechargeable battery 22 (which, in certain embodiments, may be a lithium-ion rechargeable battery) of the sterilization case 10 via an external wall outlet or other power source. The power port 18 and power adapter 18a are limited to no exact configuration or type, with the primary consideration being that size be minimized to maximize portability. Thus, the sterilization case 10 may be taken to, for example, school or work so that patients may sterilize their oral appliances while travelling and re-charge the case 10 whenever an electrical outlet is available for use.

As an additional, optional source of electricity, a battery charger 20 may be provided, which even further increases the portability of the case 10. The battery charger 20 includes male snap connectors 20b that connect to respective female snap connectors 20a to detachably retain the battery charger 20 on the bottom portion 10b of the sterilization case 10. A battery access panel 20c may be selectively removed to insert and replace a battery (not shown), such as a 9 volt battery, for charging the sterilization case 10. Battery electrical contacts 20d electrically connect the battery charger 20 to the sterilization case 10. This design allows the sterilization case 10 to be used even when a wall charger or other external power source may not be available, which is very often the circumstance when an individual is in transit.

Figure 7:
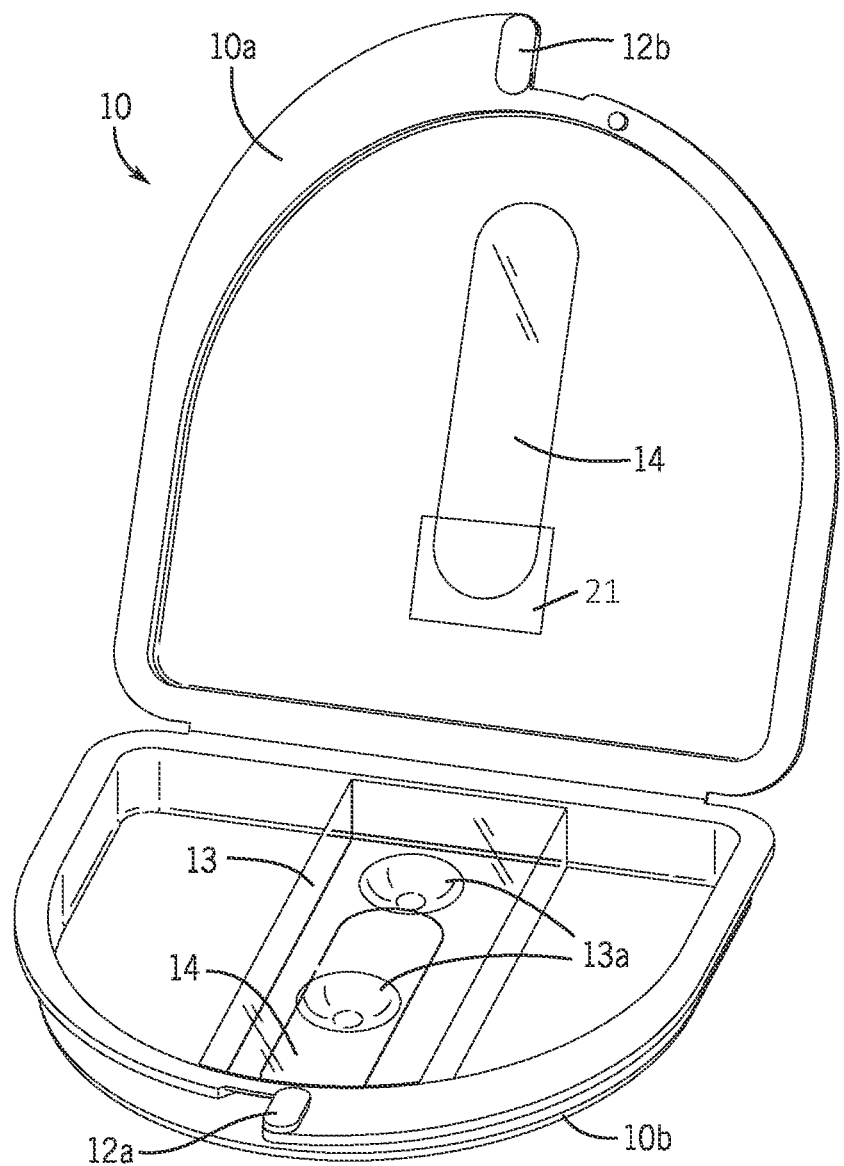
FIG. 7 is a perspective view of the embodiment of the present invention, in an open orientation and showing an optional accessory.

Contact lenses may suffer from the same sanitization problems as the ones described above with respect to oral appliances. In accordance with embodiments of the present invention, as shown in FIG. 7, a transparent accessory attachment 13 may be provided to sterilize contact lenses. The accessory attachment 13 may include recesses 13a to retain the contact lenses. As shown in FIG. 7, the accessory attachment 13 is sized to fit within the larger sterilization case 10 and sit proximal the UV bulbs 14 for maximum sanitization effect. In even further embodiments, the teachings of the present invention may be applied to provide for sanitization of other small accessories/articles, such as hearing aids.

Methods of making the present invention are already readily apparent from the above disclosure; however, a further method may include the following. A case (which may be plastic) is fabricated, and UV (e.g., UVC) bulbs are mounted inside the case. The power button 11 and other electrical components are assembled and embedded in the case, with one or more ports being disposed for charging the case in one or more ways (such as wall charging and charging via a battery) for additional portability and functionality.

A method of using the present invention may include the following. First, a user charges the case at home and takes the case to clean his/her oral device or other appliance when he/she is travelling, at school, at work or another remote location (e.g., away from home). To sterilize the oral appliance, the user would remove the oral appliance from his/her mouth and open the sterilization case via the closure tabs 12a, 12b. The oral appliance is then placed in the sterilization case 10, and the top 10a shut. Pressing the power button 11 turns on the UV bulbs and initiates a sanitization cycle. Once this cycle has ended, the oral appliance may be safely removed from the sterilization case.

The present invention has been described in terms of exemplary embodiments solely for the purpose of illustration. Persons skilled in the art will recognize from this description that the invention is not limited to the embodiments described but may be practiced with modifications and alterations limited only by the spirit and scope of the appended claims.

In the following claims, any labelling of elements, limitations, steps, or other parts of a claim (for example, first, second, etc., (a), (b), (c), etc., or (i), (ii), (iii), etc.) is only for purposes of clarity, and are not to be interpreted as suggesting any sort of ordering or precedence of the claim parts so labelled. If any such ordering or precedence is intended, it will be explicitly recited in the claim or, in some instances, it will be implicit or inherent based on the specific content of the claim. To further aid the USPTO and any readers of any patent issued on this application, it is additionally noted that there is no intent any of the appended claims to invoke paragraph (f) of 35 U.S.C. § 112 as it exists on the date of filing hereof unless the words "means for" or "step for" are explicitly used in the particular claim.

What is claimed is:

1. A method of sterilizing an oral appliance, the method comprising;
  providing a sterilization case comprising:
    a case body including a top portion and a bottom portion movably connected to one another, the case body being sized to house an oral appliance;
    a rechargeable battery;
  at least one ultraviolet light mounted in the case body and being powered by the rechargeable battery, the at least one ultraviolet light being configured to sterilize the oral appliance; and
    a transparent accessory attachment configured to sit within the case body proximal to the at least one ultraviolet light;
  opening the sterilization case;
  removing the transparent accessory attachment;
  inserting the oral appliance;
  closing the sterilization case; and
  inserting the sterilization case into a pant pocket.

* * * * *